United States Patent
Niesten et al.

(10) Patent No.: US 9,364,577 B2
(45) Date of Patent: Jun. 14, 2016

(54) HYDROPHILIC POLYURETHANE FOAM WITH LOW VOLUME SWELLING

(75) Inventors: Meike Niesten, Köln (DE); Sebastian Dörr, Düsseldorf (DE); Sascha Plug, Leverkusen (DE); Jan Schönberger, Haan (DE)

(73) Assignee: Covestro Deutschland AG, Leverkusen (DE)

( * ) Notice: Subject to any disclaimer, the term of this patent is extended or adjusted under 35 U.S.C. 154(b) by 161 days.

(21) Appl. No.: 14/115,116

(22) PCT Filed: Apr. 30, 2012

(86) PCT No.: PCT/EP2012/057932
§ 371 (c)(1),
(2), (4) Date: Dec. 30, 2013

(87) PCT Pub. No.: WO2012/150224
PCT Pub. Date: Nov. 8, 2012

(65) Prior Publication Data
US 2014/0107243 A1    Apr. 17, 2014

(30) Foreign Application Priority Data
May 4, 2011   (EP) .................................... 11164764

(51) Int. Cl.
| A61L 15/26 | (2006.01) |
| A61L 15/42 | (2006.01) |
| B82Y 30/00 | (2011.01) |
| C08G 18/08 | (2006.01) |
| C08G 18/10 | (2006.01) |
| C08G 18/12 | (2006.01) |
| C08G 18/28 | (2006.01) |
| C08G 18/44 | (2006.01) |
| C08G 18/48 | (2006.01) |
| C08G 18/72 | (2006.01) |
| C08G 18/73 | (2006.01) |
| C08G 18/75 | (2006.01) |
| C08G 18/79 | (2006.01) |
| C08L 75/04 | (2006.01) |
| A61F 13/02 | (2006.01) |
| C08G 101/00 | (2006.01) |

(52) U.S. Cl.
CPC ............ *A61L 15/26* (2013.01); *A61F 13/0206* (2013.01); *A61L 15/425* (2013.01); *B82Y 30/00* (2013.01); *C08G 18/0828* (2013.01); *C08G 18/10* (2013.01); *C08G 18/12* (2013.01); *C08G 18/283* (2013.01); *C08G 18/44* (2013.01); *C08G 18/4837* (2013.01); *C08G 18/4854* (2013.01); *C08G 18/722* (2013.01); *C08G 18/73* (2013.01); *C08G 18/755* (2013.01); *C08G 18/792* (2013.01); *C08G 18/798* (2013.01); *C08L 75/04* (2013.01); *C08G 2101/0008* (2013.01); *C08G 2101/0058* (2013.01); *C08G 2101/0066* (2013.01); *C08G 2101/0083* (2013.01)

(58) Field of Classification Search
CPC ...... C08J 9/0066; A61L 15/26; A61L 15/425; A61L 15/16; C08G 18/10; C08G 18/12; C08G 18/44283; C08G 18/722; C08G 18/798; C08G 18/4854; C08G 18/4837; C08G 18/8064; C08G 18/73; C08G 18/755; C08G 18/792; C08G 18/082; C08G 2101/0008; C08G 2101/0058; C08G 2101/0066; C08G 2101/0083; C08L 75/04; A61F 13/0206; B82Y 30/00
See application file for complete search history.

(56) References Cited

U.S. PATENT DOCUMENTS

| 4,108,814 | A |   | 8/1978 | Reiff et al. |
| 4,137,200 | A | * | 1/1979 | Wood et al. ................... 521/159 |
| 4,299,924 | A | * | 11/1981 | Nomura et al. ............... 521/131 |
| 5,844,013 | A |   | 12/1998 | Kenndoff et al. |
| 6,051,622 | A | * | 4/2000 | Kinkelaar et al. ............ 521/159 |
| 2004/0034162 | A1 |   | 2/2004 | Laas et al. |
| 2008/0107718 | A1 |   | 5/2008 | Baron et al. |
| 2009/0054542 | A1 | * | 2/2009 | Schoenberger ............... 521/137 |
| 2009/0216168 | A1 |   | 8/2009 | Eckstein |
| 2011/0184080 | A1 |   | 7/2011 | Schonberger et al. |

FOREIGN PATENT DOCUMENTS

| CA | 2253119 A1 | 5/1999 |
| DE | 2446440 A1 | 4/1976 |
| EP | 0335669 A2 | 10/1989 |
| EP | 916647 A2 | 5/1999 |
| EP | 1815875 A1 | 8/2007 |

(Continued)

OTHER PUBLICATIONS

International Search Report for PCT/EP2012/057932 mailed Jul. 31, 2012.

*Primary Examiner* — John Cooney
(74) *Attorney, Agent, or Firm* — Drinker Biddle & Reath LLP

(57) ABSTRACT

The invention relates to a specific composition comprising A) isocyanate-functional prepolymers obtainable by reaction of A1) aliphatic diisocyanates with A2) di- to hexa-functional polyalkylene oxides having an ethylene oxide content of 50 to 100 mol %, based on the total amount of the oxyalkylene groups present, B) an aqueous polyurethane suspension, an aqueous polyacrylate suspension or aqueous silica sols, especially for production of hydrophilic, aliphatic polyurethane foams. The invention further provides a process for producing a hydrophilic, aliphatic polyurethane foam, based on the inventive composition, a polyurethane foam obtainable by the process and a wound dressing comprising the polyurethane foam.

16 Claims, No Drawings

(56) References Cited

FOREIGN PATENT DOCUMENTS

| EP | 1923077 | A1 | 5/2008 |
| EP | 2143744 | A1 | 1/2010 |
| WO | WO-94/07935 | A1 | 4/1994 |
| WO | WO-98/17328 | A1 | 4/1998 |
| WO | WO-00/39181 | A1 | 7/2000 |
| WO | WO-01/88006 | A1 | 11/2001 |

* cited by examiner

HYDROPHILIC POLYURETHANE FOAM WITH LOW VOLUME SWELLING

RELATED APPLICATIONS

This application is a national stage application (under 35 U.S.C. §371) of PCT/EP2012/057932, filed Apr. 30, 2012, which claims benefit of European Application No. 11164764.0, filed May 4, 2011, which is incorporated by reference herein.

The present invention relates to a specific composition, which can be used in particular for producing hydrophilic aliphatic polyurethane foams. The present invention further relates to a process for producing a hydrophilic aliphatic polyurethane foam based on the composition of the present invention, to a polyurethane foam obtainable by said process and also to a wound dressing comprising said polyurethane foam.

European patent application EP 2 143 744 A1 describes hydrophilic aliphatic polyurethane foams obtainable by reacting low-monomer prepolymers with water. The absorbence of these foams for liquids such as water is high, but so is also their volume swelling response, i.e., there is an appreciable increase in foam volume in the course of liquid imbibition. This is particularly disadvantageous when the foams are used in wound dressings, since the increased volume causes the wound dressing deform. An undesirable exertion of pressure on the wound can occur as a result of this deformation. In the worst case, all of the wound dressing becomes detached.

The problem addressed by the present invention was accordingly that of providing a composition for producing a polyurethane foam which has high absorbence for liquids such as water coupled with only a minimal volume swelling response.

This problem is solved according to the present invention by a composition comprising
A) isocyanate-functional prepolymers obtainable by reaction of
  A1) aliphatic diisocyanates with
  A2) di- to hexafunctional polyalkylene oxides having an ethylene oxide fraction of 50 to 100 mol %, based on the total amount of oxyalkylene groups present,
B) an aqueous polyurethane suspension, an aqueous polyacrylate suspension or aqueous silica sols.

It has transpired that using the composition provides a polyurethane foam having high absorbence for liquids such as water coupled with only a minimal volume swelling response.

An aqueous suspension within the meaning of the present invention is a heterogeneous mixture of a particulate solid (disperse phase) in a water-containing liquid phase (dispersing medium) where the average diameter of the disperse phase, as determined by laser correlation spectroscopy, is in the range from 1 to 1000 nm, preferably in the range from 2 to 800 nm, more preferably in the range from 5 to 500 nm and even more preferably in the range from 20 to 400 nm. It is likewise preferable for the dispersing medium to consist exclusively of water.

In a preferred embodiment of the present invention, the aliphatic diisocyanates A1) have a molar mass of 140 to 278 g/mol.

Examples of suitable aliphatic diisocyanates A1) are hexamethylene diisocyanate (HDI), isophorone diisocyanate (IPDI), butylene diisocyanate (BDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, of which hexamethylene diisocyanate, isophorone diisocyanate, butylene diisocyanate and bis(isocyanatocyclohexyl)methane are preferred. Butylene diisocyanate, hexamethylene diisocyanate, and isophorone diisocyanate are particularly preferred and hexamethylene diisocyanate and isophorone diisocyanate are very particularly preferred.

It is also advantageous for the di- to hexafunctional polyalkylene oxides A2) to have an OH number in the range from 22.5 to 112.

The polyalkylene oxides may particularly also have an ethylene oxide content of 50 to 100 mol %, preferably of 60 to 85 mol %, based on the total amount of oxyalkylene groups present.

The number-average molecular weights of the polyalkylene oxides are typically in the range from 1000 to 15 000 g/mol, and preferably in the range from 3000 to 8500 g/mol.

The polyalkylene oxides of component A2) preferably further have OH functionalities of 2 to 6, more preferably of 3 to 6 and even more preferably of 3 to 4.

Suitable polyalkylene oxides include, for example, copolymers of ethylene oxide and propylene oxide.

It is also particularly preferable for the polyalkylene oxides to be started on polyols or amines. Suitable starters are glycerol, trimethylolpropane (TMP), sorbitol, pentaerythritol, triethanolamine, ammonia or ethylenediamine.

The isocyanate-functional prepolymers A) are prepared by typically adjusting the ratio of the polyalkylene oxides A2) to the low molecular weight aliphatic diisocyanates A1) such that there are from 2 to 20 mol, preferably from 2 to 10 mol and more preferably from 5 to 10 mol of NCO groups of the low molecular weight aliphatic diisocyanate A1) per 1 mol of OH groups of the polyalkylene oxide A2).

The prepolymers can be prepared in the presence of urethanization catalysts such as tin compounds, zinc compounds, amines, guanidines or amidines, or in the presence of allophanatization catalysts such as zinc compounds.

The temperature for reacting the polyalkylene oxides A2) with the diisocyanates A1) to form the prepolymer A) is typically in the range from 25 to 140° C., and preferably in the range from 60 to 100° C.

When excess diisocyanate was used in the reaction, thin film distillation may preferably be used to remove the unconverted remainder afterwards.

Before, during and after reacting the diisocyanates with the polyalkylene oxides or removing excess diisocyanate by distillation, acidic or alkylating stabilizers, such as benzoyl chloride, isophthaloyl chloride, methyl tosylate, chloropropionic acid, HCl or antioxidants such as di-tert-butylcresol or tocopherol may be added.

The employed prepolymers A) preferably have a residual monomer content of below 0.5 wt %, based on the prepolymer. This content can be achieved through appropriately selected starting quantities for the diisocyanates A1) and the polyalkylene oxides A2). However, it is preferable for diisocyanate A1) to be used in excess and unconverted monomers to be separated off afterwards, preferably by distillation.

The NCO content of isocyanate-functional prepolymers A) is preferably in the range from 1.5 to 4.5 wt %, more preferably in the range from 1.5 to 3.5 wt % and most preferably in the range from 1.5 to 3.0 wt %.

Aqueous suspension B) may be an organic suspension or an inorganic suspension, i.e., comprise organic or inorganic particles of a solid material as disperse phase. Examples of such suspensions B) are aqueous polyurethane suspensions, aqueous polyacrylate suspensions and aqueous silica sols. However, aqueous polyurethane suspensions are particularly preferred, and they may be in an anionically hydrophilicized state in particular.

It is very particularly preferable for the composition according to the present invention to contain an aqueous, anionically hydrophilicized polyurethane suspension B) which is obtainable by preparing J) isocyanate-functional prepolymers from
   J1) organic polyisocyanates,
   J2) polymeric polyols especially with number-average molecular weights of 400 to 8000 g/mol and/or OH functionalities of 1.5 to 6,
   J3) optionally hydroxyl-functional compounds, especially with molecular weights of 62 to 399 g/mol, and
   J4) optionally isocyanate-reactive, anionic or potentially anionic and/or optionally nonionic hydrophilicizing agents, chain extending said isocyanate-functional prepolymers J) by complete or partial reaction of their free NCO groups with
   K1) isocyanate-reactive, preferably amino-functional, anionic or potentially anionic hydrophilicizing agents, and/or
   K2) optionally amino-functional compounds, especially with molecular weights of 32 to 400 g/mol, and dispersing said prepolymers J) in water before, during or after said chain-extending reaction, wherein any potentially anionic groups present are converted into the anionic form by partial or complete reaction with a neutralizing agent.

To obtain an anionic hydrophilicization, hydrophilicizing agents should be used in J4) and/or K1) which have at least one NCO-reactive group such as amino, hydroxyl or thiol groups and also —$COO^-$ or —$SO_3^-$ or —$PO_3^{2-}$ as anionic groups or their wholly or partly protonated acidic forms as potentially anionic groups.

Preferred aqueous anionic polyurethane suspensions B) have a low degree of hydrophilic anionic groups, preferably from 0.1 to 15 milliequivalents per 100 g of solid resin.

To obtain good stability to sedimentation, the number-average particle size of advantageous polyurethane suspensions is preferably less than 750 nm and more preferably less than 550 nm, as determined using laser correlation spectroscopy.

The ratio of NCO groups on compounds from component J1) to NCO-reactive groups such as amino, hydroxyl or thiol groups on compounds of components J2) to J4) in the preparation of NCO-functional prepolymer J) is in the range from 1.05 to 3.5, preferably in the range from 1.2 to 3.0 and more preferably in the range from 1.3 to 2.5.

The amino-functional compounds in stage K1) are preferably used in such an amount that the equivalent ratio of isocyanate-reactive amino groups of these compounds to the free isocyanate groups of the prepolymer is in the range from 40 to 150%, preferably between 50 to 125% and more preferably between 60 to 120%.

Suitable polyisocyanates of component J1) are the familiar aromatic, araliphatic, aliphatic or cycloaliphatic polyisocyanates with NCO functionality ≥2.

Examples of such suitable polyisocyanates are 1,4-butylene diisocyanate, 1,6-hexamethylene diisocyanate (HDI), isophorone diisocyanate (IPDI), 2,2,4- and/or 2,4,4-trimethylhexamethylene diisocyanate, the isomeric bis(4,4'-isocyanatocyclohexyl)-methanes or their mixtures of any desired isomer content, 1,4-cyclohexylene diisocyanate, 1,4-phenylene diisocyanate, 2,4- and/or 2,6-tolylene diisocyanate, 1,5-naphthylene diisocyanate, 2,2'- and/or 2,4'- and/or 4,4'-diphenylmethane diisocyanate, 1,3- and/or 1,4-bis(2-isocyanatoprop-2-yl)benzene (TMXDI), 1,3-bis(isocyanatomethyl)benzene (XDI), alkyl 2,6-diisocyanatohexanoate (lysine diisocyanates) with C1-C8 alkyl groups, and also 4-isocyanatomethyl-1,8-octane diisocyanate (nonane triisocyanate) and triphenylmethane 4,4',4"-triisocyanate.

As well as the aforementioned polyisocyanates, it is also possible to use proportions of modified diisocyanates or triisocyanates of uretdione, isocyanurate, urethane, allophanate, biuret, iminooxadiazinedione and/or oxadiazinetrione structure.

Preferably, the polyisocyanates or polyisocyanate mixtures of the aforementioned kind have exclusively aliphatically and/or cycloaliphatically attached isocyanate groups and an average NCO functionality in the range from 2 to 4, preferably in the range from 2 to 2.6 and more preferably in the range from 2 to 2.4, for the mixture.

It is particularly preferable for J1) to utilize 1,6-hexamethylene diisocyanate, isophorone diisocyanate, the isomeric bis (4,4'-isocyanatocyclohexyl)methanes, and also mixtures thereof.

J2) utilizes polymeric polyols having a number average molecular weight Mn of preferably from 400 to 8000 g/mol and more preferably from 600 to 3000 g/mol. These preferably have an OH functionality in the range from 1.8 to 3 and more preferably in the range from 1.9 to 2.1.

Suitable polymeric polyols are the well-known polyurethane coating technology polyester polyols, polyacrylate polyols, polyurethane polyols, polycarbonate polyols, polyether polyols, polyester polyacrylate polyols, polyurethane polyacrylate polyols, polyurethane polyester polyols, polyurethane polyether polyols, polyurethane polycarbonate polyols and polyester polycarbonate polyols. These can be used in J2) individually or in any desired mixtures with each or one another.

Examples of suitable polyester polyols are the well-known polycondensates formed from di- and also optionally tri- and tetraols and di- and also optionally tri- and tetracarboxylic acids or hydroxycarboxylic acids or lactones. Instead of the free polycarboxylic acids it is also possible to use the corresponding polycarboxylic anhydrides or corresponding polycarboxylic esters of lower alcohols for preparing the polyesters.

Suitable diols for the preparation are ethylene glycol, butylene glycol, diethylene glycol, triethylene glycol, polyalkylene glycols such as polyethylene glycol, also 1,2-propanediol, 1,3-propanediol, butanediol(1,3), butanediol(1,4), hexanediol(1,6) and isomers, neopentyl glycol or neopentyl glycol hydroxypivalate, of which hexanediol(1,6) and isomers, neopentyl glycol and neopentyl glycol hydroxypivalate are preferred. Besides these it is also possible to use polyols such as trimethylolpropane, glycerol, erythritol, pentaerythritol, trimethylolbenzene or trishydroxyethyl isocyanurate.

Useful dicarboxylic acids include phthalic acid, isophthalic acid, terephthalic acid, tetrahydrophthalic acid, hexahydrophthalic acid, cyclohexanedicarboxylic acid, adipic acid, azelaic acid, sebacic acid, glutaric acid, tetrachlorophthalic acid, maleic acid, fumaric acid, itaconic acid, malonic acid, suberic acid, 2-methylsuccinic acid, 3,3-diethylglutaric acid and/or 2,2-dimethylsuccinic acid. The corresponding anhydrides can also be used as a source of an acid.

When the average functionality of the polyol to be esterified is > than 2, monocarboxylic acids, such as benzoic acid and hexanecarboxylic acid can also be used in addition.

Preferred acids are aliphatic or aromatic acids of the aforementioned kind. Adipic acid, isophthalic acid and optionally trimellitic acid are particularly preferred.

Hydroxycarboxylic acids useful as reaction participants in the preparation of a polyester polyol having terminal hydroxyl groups include for example hydroxycaproic acid, hydroxybutyric acid, hydroxydecanoic acid, hydroxystearic acid and the like. Suitable lactones are caprolactone, butyrolactone and homologs. Caprolactone is preferred.

J2) may likewise utilize hydroxyl-containing polycarbonates, preferably polycarbonate diols, more preferably having number average molecular weights Mn in the range from 400 to 8000 g/mol and most preferably in the range from 600 to 3000 g/mol. These are obtainable by reaction of carbonic acid derivatives, such as diphenyl carbonate, dimethyl carbonate or phosgene, with polyols, preferably diols. Examples of such diols are ethylene glycol, 1,2-propanediol, 1,3-propanediol, 1,3-butanediol, 1,4-butanediol, 1,6-hexanediol, 1,8-octanediol, neopentyl glycol, 1,4-bishydroxymethylcyclohexane, 2-methyl-1,3-propanediol, 2,2,4-trimethylpentanediol-1,3, dipropylene glycol, polypropylene glycols, dibutylene glycol, polybutylene glycols, bisphenol A and lactone-modified diols of the aforementioned kind.

The polycarbonate diol preferably contains from 40 to 100 wt % of hexanediol, in particular 1,6-hexanediol and/or hexanediol derivatives, based on the underlying diols. Such hexanediol derivatives are based on hexanediol and have ester or ether groups as well as terminal OH groups. Such derivatives are obtainable by reaction of hexanediol with excess caprolactone or by etherification of hexanediol with itself to form di- or trihexylene glycol.

In lieu of or in addition to pure polycarbonate diols, polyether-polycarbonate diols can also be used in J2).

Hydroxyl-containing polycarbonates preferably have a linear construction.

J2) may likewise utilize polyether polyols. Useful polyether polyols include for example the well-known polyurethane chemistry polytetramethylene glycol polyethers obtainable by polymerization of tetrahydrofuran via cationic ring opening.

Useful polyether polyols likewise include the well-known addition products of styrene oxide, ethylene oxide, propylene oxide, butylene oxides and/or epichlorohydrin onto di- or polyfunctional starter molecules.

Useful starter molecules include all prior art compounds, for example water, butyl diglycol, glycerol, ethylene glycol, trimethylolpropane, propylene glycol, sorbitol, ethylenediamine, triethanolamine, 1,4-butanediol. Preferred starter molecules are water, ethylene glycol, propylene glycol, 1,4-butanediol, diethylene glycol and butyl diglycol.

Particularly preferable polyurethane suspensions B) contain as component J2) a mixture of polycarbonate polyols and polytetramethylene glycol polyols wherein, in this mixture, the proportion of polycarbonate polyols can preferably be 20 to 80 wt % and the proportion of polytetramethylene glycol polyols can preferably be 80 to 20 wt %. More preference is given to a 30 to 75 wt % proportion of polytetramethylene glycol polyols and a 25 to 70 wt % proportion of polycarbonate polyols. Most preference is given to a 35 to 70 wt % proportion of polytetramethylene glycol polyols and a 30 to 65 wt % proportion of polycarbonate polyols, each subject to the proviso that the sum total of the weight percentages for the polycarbonate and polytetramethylene glycol polyols is 100% and the proportion of component J2) which is accounted for by the sum total of the polycarbonate and polytetramethylene glycol polyether polyols is at least 50 wt %, preferably 60 wt % and more preferably at least 70 wt %.

J3) may optionally utilize hydroxyl-functional compounds such as polyols of the recited molecular weight range that have up to 20 carbon atoms, such as ethylene glycol, diethylene glycol, triethylene glycol, 1,2-propanediol, 1,3-propanediol, 1,4-butanediol, 1,3-butylene glycol, cyclohexanediol, 1,4-cyclohexanedimethanol, 1,6-hexanediol, neopentyl glycol, hydroquinone dihydroxyethyl ether, bisphenol A (2,2-bis(4-hydroxyphenylpropane), hydrogenated bisphenol A, (2,2-bis(4-hydroxycyclohexyl)propane), trimethylolpropane, glycerol, pentaerythritol and also any desired mixtures thereof with each or one another.

Also suitable are ester diols of the recited molecular weight range such as α-hydroxybutyl-ε-hydroxycaproic ester, ω-hydroxyhexyl-γ-hydroxybutyric ester, β-hydroxyethyl adipate or bis(β-hydroxyethyl)terephthalate.

J3) may further utilize monofunctional hydroxyl-containing compounds. Examples of such monofunctional compounds are ethanol, n-butanol, ethylene glycol monobutyl ether, diethylene glycol monomethyl ether, ethylene glycol monobutyl ether, diethylene glycol monobutyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, tripropylene glycol monobutyl ether, 2-ethylhexanol, 1-octanol, 1-dodecanol, 1-hexadecanol.

Particularly preferred compounds of component J3) are 1,6-hexanediol, 1,4-butanediol, neopentyl glycol and trimethylolpropane.

An anionically or potentially anionically hydrophilicizing compound for component J4) is any compound which has at least one isocyanate-reactive group such as a hydroxyl group and also at least one functionality such as for example —COO$^-$M$^+$, —SO$_3^-$M$^+$, —PO(O$^-$M$^+$)$_2$ where M$^+$ is for example a metal cation, H$^+$, NH$_4^+$, NHR$_3^+$, where R in each occurrence may be C1-C12 alkyl, C5-C6 cycloalkyl and/or C2-C4 hydroxyalkyl, which functionality interacts with aqueous media by entering a pH-dependent dissociative equilibrium and thereby can have a negative or neutral charge. Suitable anionically or potentially anionically hydrophilicizing compounds are mono- and dihydroxycarboxylic acids, mono- and dihydroxysulfonic acids, and also mono- and dihydroxyphosphonic acids and salts thereof. Examples of such anionic or potentially anionic hydrophilicizing agents are dimethylolpropionic acid, dimethylolbutyric acid, hydroxypivalic acid, malic acid, citric acid, glycolic acid, lactic acid and the propoxylated adduct formed from 2-butenediol and NaHSO$_3$, as described in DE-A 2 446 440, page 5-9, formula I-III. Preferred anionic or potentially anionic hydrophilicizing agents for component J4) are those of the aforementioned kind that have carboxylate or carboxyl groups and/or sulfonate groups.

Particularly preferred anionic or potentially anionic hydrophilicizing agents for component J4) are those which contain carboxylate/carboxylic acid groups as ionic or potentially ionic groups, such as dimethylolpropionic acid, dimethylolbutyric acid and hydroxypivalic acid and salts thereof.

Suitable nonionically hydrophilicizing compounds for component J4) are for example polyoxyalkylene ethers that contain at least one hydroxyl or amino group, preferably at least one hydroxyl group.

Examples are the monohydroxy-functional polyalkylene oxide polyether alcohols containing on average from 5 to 70 and preferably from 7 to 55 ethylene oxide units per molecule and obtainable in a conventional manner by alkoxylation of suitable starter molecules (for example in Ullmanns Encyclopädie der technischen Chemie, 4$^{th}$ edition, volume 19, Verlag Chemie, Weinheim pages 31-38).

These compounds are either pure polyethylene oxide ethers or mixed polyalkylene oxide ethers, in which case they then preferably contain at least 30 mol % and more preferably at least 40 mol % of ethylene oxide units, based on all alkylene oxide units present.

Very particularly preferred nonionic compounds are monofunctional mixed polyalkylene oxide polyethers having 40 to 100 mol % of ethylene oxide units and 0 to 60 mol % of propylene oxide units.

Suitable starter molecules for such nonionic hydrophilicizing agents are saturated monoalcohols such as methanol, ethanol, n-propanol, isopropanol, n-butanol, isobutanol, sec-butanol, the isomeric pentanols, hexanols, octanols and nonanols, n-decanol, n-dodecanol, n-tetradecanol, n-hexadecanol, n-octadecanol, cyclohexanol, the isomeric methylcyclohexanols or hydroxymethylcyclohexane, 3-ethyl-3-hydroxymethyloxetane or tetrahydrofurfuryl alcohol, diethylene glycol monoalkyl ethers, for example diethylene glycol monobutyl ether, unsaturated alcohols such as allyl alcohol, 1,1-dimethylallyl alcohol or oleic alcohol, aromatic alcohols such as phenol, the isomeric cresols or methoxyphenols, araliphatic alcohols such as benzyl alcohol, anise alcohol or cinnamyl alcohol, secondary monoamines such as dimethylamine, diethylamine, dipropylamine, diisopropylamine, dibutylamine, bis(2-ethylhexyl)amine, N-methyl- and N-ethylcyclohexylamine or dicyclo-hexylamine and also heterocyclic secondary amines such as morpholine, pyrrolidine, piperidine or 1H-pyrazole. Preferred starter molecules are saturated monoalcohols of the aforementioned kind. Particular preference is given to using diethylene glycol monobutyl ether or n-butanol as starter molecules.

Suitable alkylene oxides for the alkoxylation reaction are in particular ethylene oxide and propylene oxide, which can be used in the alkoxylation reaction in any desired order or else in admixture.

An anionically or potentially anionically hydrophilicizing compound for component K1) is any compound which has at least one isocyanate-reactive group, preferably an amino group, and also at least one functionality such as for example —COO$^-$M$^+$, —SO$_3^-$M$^+$, —PO(O$^-$M$^+$)$_2$ where M$^+$ is for example a metal cation, H$^+$, NH$_4^+$, NHR$_3^+$, where R in each occurrence may be C1-C12 alkyl, C5-C6 cycloalkyl and/or C2-C4 hydroxyalkyl, which functionality interacts with aqueous media by entering a pH-dependent dissociative equilibrium and thereby can have a negative or neutral charge.

Suitable anionically or potentially anionically hydrophilicizing compounds K1) are mono- and diaminocarboxylic acids, mono- and diaminosulfonic acids and also mono- and diaminophosphonic acids and salts thereof. Examples of such anionic or potentially anionic hydrophilicizing agents are N-(2-aminoethyl)-β-alanine, 2-(2-aminoethylamino)ethane-sulfonic acid, ethylenediaminepropylsulfonic acid, ethylenediaminebutylsulfonic acid, 1,2- or 1,3-propylenediamine-β-ethylsulfonic acid, glycine, alanine, taurine, lysine, 3,5-diaminobenzoic acid and the addition product of IPDA and acrylic acid (EP-A 0 916 647, Example 1). It is further possible to use cyclohexylaminopropanesulfonic acid (CAPS) from WO-A 01/88006 as anionic or potentially anionic hydrophilicizing agent.

Preferred anionic or potentially anionic hydrophilicizing agents for component K1) are those of the aforementioned kind that have carboxylate or carboxylic acid groups and/or sulfonate groups, such as the salts of N-(2-aminoethyl)-β-alanine, of 2-(2-aminoethylamino)ethane-sulfonic acid or of the addition product of IPDA and acrylic acid (EP-A 0 916 647, Example 1).

Mixtures of anionic or potentially anionic hydrophilicizing agents and nonionic hydrophilicizing agents can also be used for hydrophilicization.

Component K2) may utilize di- or polyamines such as 1,2-ethylenediamine, 1,2-diaminopropane, 1,3-diaminopropane, 1,4-diaminobutane, 1,6-diaminohexane, isophoronediamine, isomeric mixture of 2,2,4- and 2,4,4-trimethylhexamethylenediamine, 2-methylpenta-methylenediamine, diethylenetriamine, triaminononane, 1,3-xylylenediamine, 1,4-xylylenediamine, α,α,α',α'-tetramethyl-1,3-xylylenediamine, α,α,α',α'-tetramethyl-1,4-xylylenediamine and 4,4-diaminodicyclohexylmethane and/or dimethylethylenediamine. It is likewise possible but less preferable to use hydrazine or and also hydrazides such as adipohydrazide.

Component K2) can further utilize compounds which as well as a primary amino group also have secondary amino groups or which as well as an amino group (primary or secondary) also have OH groups. Examples thereof are primary/secondary amines, such as diethanolamine, 3-amino-1-methylaminopropane, 3-amino-1-ethylaminopropane, 3-amino-1-cyclohexylaminopropane, 3-amino-1-methylaminobutane, alkanolamines such as N-aminoethylethanolamine, ethanolamine, 3-aminopropanol, neopentanolamine.

Component K2) can further also utilize monofunctional isocyanate-reactive amine compounds, for example methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine, or suitable substituted derivatives thereof, amide-amines formed from diprimary amines and monocarboxylic acids, monoketimes of diprimary amines, primary/tertiary amines, such as N,N-dimethylaminopropylamine.

Preferred compounds for component K2) are 1,2-ethylenediamine, 1,4-diaminobutane and isophoronediamine.

In a further preferred embodiment, components J1) to J4) and K1) to K2) are used in the following amounts, with the individual amounts always adding up to 100 wt %:
5 to 40 wt % of component J1),
55 to 90 wt % of component J2),
0.5 to 20 wt % of total components J3) and K1),
0.1 to 25 wt % of total components J4) and K2),
wherein based on the total amounts of components J1) to J4) and K1) to K2) from 0.1 to 5 wt % of anionic or potentially anionic hydrophilicizing agents J4) and/or K2) is used.

In a particularly preferred embodiment of polyurethane suspensions B), components J1) to J4) and K1) to K2) are used in the following amounts, with the individual amounts always adding up to 100 wt %:
5 to 35 wt % of component J1),
60 to 90 wt % of component J2),
0.5 to 15 wt % of total components J3) and K1),
0.1 to 15 wt % of total components J4) and K2),
wherein based on the total amounts of components J1) to J4) and K1) to K2) from 0.2 to 4 wt % of anionic or potentially anionic hydrophilicizing agents J4) and/or K2) is used.

In a very particularly preferred embodiment of the polyurethane suspensions, components J1) to J4) and K1) to K2) are used in the following amounts, with the individual amounts always adding up to 100 wt %:
10 to 30 wt % of component J1),
65 to 85 wt % of component J2),
0.5 to 14 wt % of total components J3) and K1),
0.1 to 13.5 wt % of total components J4) and K2),
wherein based on the total amounts of components J1) to J4) and K1) to K2) from 0.5 to 3.0 wt % of anionic or potentially anionic hydrophilicizing agents J4) and/or K2) is used.

The production of the anionically hydrophilicized polyurethane suspensions B) can be carried out in one or more stages in homogeneous phase or, in the case of a multistage reaction, partly in disperse phase. After completely or partially conducted polyaddition from J1) to J4), a dispersing, emulsifying or dissolving step is carried out. This is followed if appropriate by a further polyaddition or modification in disperse or dissolved (homogeneous) phase.

Any prior art process such as for example the prepolymer mixing process, the acetone process or the melt dispersing process can be used therefor. The acetone process is preferred.

Production by the acetone process typically involves the constituents J2) to J4) and the polyisocyanate component J1) being wholly or partly introduced as an initial charge to produce an isocyanate-functional polyurethane prepolymer and optionally diluted with a water-miscible but isocyanate-inert solvent and heated to temperatures in the range from 50 to 120° C. The isocyanate addition reaction can be speeded using the catalysts known in polyurethane chemistry.

Useful solvents include the customary aliphatic, keto-functional solvents such as acetone or 2-butanone, which can be added not just at the start of the production process but also later, optionally in portions. Acetone and 2-butanone are preferred.

Other solvents such as xylene, toluene, cyclohexane, butyl acetate, methoxypropyl acetate, N-methylpyrrolidone, N-ethylpyrrolidone, solvents having ether or ester units can additionally be used and wholly or partly distilled off or in the case of N-methylpyrrolidone, N-ethylpyrrolidone remain completely in the suspension. But preference is given to not using any other solvents apart from the customary aliphatic, keto-functional solvents.

In the production of the polyurethane prepolymer from J1) to J4), the amount of substance ratio of isocyanate groups to with isocyanate-reactive groups can be in the range from 1.05 to 3.5, preferably in the range from 1.2 to 3.0 and more preferably in the range from 1.3 to 2.5.

The reaction of components J1) to J4) to form the prepolymer is effected partially or completely, but preferably completely. Polyurethane prepolymers containing free isocyanate groups are obtained in this way, without a solvent or in solution.

The neutralizing step to effect partial or complete conversion of potentially anionic groups into anionic groups utilizes bases such as tertiary amines, for example trialkylamines having 1 to 12 and preferably 1 to 6 carbon atoms and more preferably 2 to 3 carbon atoms in every alkyl radical or alkali metal bases such as the corresponding hydroxides.

Examples thereof are trimethylamine, triethylamine, methyldiethylamine, tripropylamine, N-methylmorpholine, methyldiisopropylamine, ethyldiisopropylamine and diisopropylethylamine. The alkyl radicals may also bear for example hydroxyl groups, as in the case of the dialkylmonoalkanol-, alkyldialkanol- and trialkanolamines. Useful neutralizing agents further include if appropriate inorganic bases, such as aqueous ammonia solution, sodium hydroxide or potassium hydroxide.

Preference is given to ammonia, triethylamine, triethanolamine, dimethylethanolamine or diisopropylethylamine and also sodium hydroxide and potassium hydroxide, particular preference being given to sodium hydroxide and potassium hydroxide.

The bases are employed in an amount of substance which is in particular between 50 and 125 mol % and preferably between 70 and 100 mol % of the amount of substance of the acid groups to be neutralized. Neutralization can also be effected at the same time as the dispersing step, by including the neutralizing agent in the water of dispersion.

Subsequently, in a further process step, if this has not already been done or only to some extent, the prepolymer obtained can be dissolved with the aid of aliphatic ketones such as acetone or 2-butanone.

In the chain extension reaction, $NH_2$- and/or NH-functional components are reacted, partially or completely, with the still remaining isocyanate groups of the prepolymer. Preferably, the chain extension/termination is carried out before dispersion in water.

Chain termination is typically carried out using amines K2) having an isocyanate-reactive group such as methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine or suitable substituted derivatives thereof, amide-amines formed from diprimary amines and monocarboxylic acids, monoketimes of diprimary amines, primary/tertiary amines, such as N,N-dimethylaminopropylamine.

When partial or complete chain extension is carried out using anionic or potentially anionic hydrophilicizing agents conforming to definition K1) with $NH_2$ or NH groups, chain extension of the prepolymers is preferably carried out before dispersion.

The aminic components K1) and K2) can optionally be used in water- or solvent-diluted form individually or in mixtures, any order of addition being possible in principle.

When water or organic solvent is used as a diluent, the diluent content of the chain-extending component used in B) is preferably in the range from 70% to 95% by weight.

The dispersing/suspending step preferably takes place after chain extension. The dissolved and chain-extended polyurethane polymer is either introduced into the dispersing water, if appropriate under vigorous shearing, for example vigorous stirring, or conversely the suspending water is stirred into the chain-extended polyurethane polymer solutions. It is preferable to add the water to the dissolved chain-extended polyurethane polymer.

The organic solvent still present in the suspensions after the dispersing step is then typically removed by distillation. Removal during the dispersing step is likewise possible.

The residual level of organic solvents in the polyurethane suspensions B) is typically less than 1.0% by weight and preferably less than 0.5% by weight, based on the entire suspension.

The pH of the polyurethane suspensions B) is typically less than 9.0, preferably less than 8.5, more preferably less than 8.0 and most preferably is in the range from 6.0 to 7.5.

The solids content of polyurethane suspensions B) is typically 40 to 70, preferably 50 to 65 and more preferably 55 to 65 wt %. Further dilution of the suspension in water before use is possible, as is the use of the suspension and water as a separate constituent of the composition.

Suitable aqueous silica sols are colloidal suspensions of amorphous silica in water, which are also known as silicon dioxide sols, but usually as silica sols for short. The silicon dioxide is present therein in the form of spherical and surface-hydroxylated particles. Colloid particle diameter is generally in the range from 1 to 200 nm.

Typical aqueous polyacrylate suspensions contain for example one or more of the following construction components:
a) styrene and/or other vinylaromatic compounds,
b) acrylic esters,
c) polyvinylidene compound of functionality≥2,
d) acid-functional olefinically unsaturated monomers, e) methacrylic esters, f) olefinically unsaturated compounds other than those recited in a) to e).

Suitable vinylaromatic compounds a) especially with up to 20 carbon atoms include, for example, styrene, vinyltoluene, o-methylstyrene, p-methylstyrene, butylstyrene, decylstyrene, halogenated styrenes, for example monochlorostyrenes, dichlorostyrenes, tribromostyrenes or tetrabromostyrenes. Styrene is preferred.

Suitable acrylic esters b) comprise particularly methyl acrylate, ethyl acrylate, propyl acrylate, isopropyl acrylate, n-butyl acrylate, sec-butyl acrylate, tert-butyl acrylate, pentyl acrylate, hexyl acrylate, heptyl acrylate, octyl acrylate, 2-octyl acrylate, ethylhexyl acrylate, nonyl acrylate, 2-methyloctyl acrylate, 2-tert-butylheptyl acrylate, 3-isopropylheptyl acrylate, decyl acrylate, undecyl acrylate, 5-methylundecyl acrylate, dodecyl acrylate, 2-methyldodecyl acrylate, tridecyl acrylate, 5-methyltridecyl acrylate, tetradecyl acrylate, pentadecyl acrylate, hexadecyl acrylate, 2-methylhexadecyl acrylate, heptadecyl acrylate, 5-isopropylheptadecyl acrylate, 5-ethyloctadecyl acrylate, octadecyl acrylate, nonadecyl acrylate, eicosyl acrylate, cycloalkyl acrylates, for example cyclopentyl acrylate, cyclohexyl acrylate, 3-vinyl-2-butylcyclohexyl acrylate, cycloheptyl acrylate, cyclooctyl acrylate, bornyl acrylate, tetrahydrofurfuryl acrylate and isobornyl acrylate. Ethyl acrylate, n-butyl acrylate, ethylhexyl acrylate, cyclohexyl acrylate are preferred and ethyl acrylate, n-butyl acrylate or ethylhexyl acrylate are particularly preferred.

Suitable polyvinylidene compounds c) include polyvinylidene compounds having two or more olefinically unsaturated bonds. They include particularly acrylic or methacrylic esters of polyols with functionality $\geq 2$, e.g., ethylene glycol diacrylate, diethylene glycol diacrylate, glycerol diacrylate, glycerol triacrylate, ethylene glycol dimethacrylate, 1,3-propanediol diacrylate, 1,3-propanediol dimethacrylate, 1,4-butanediol diacrylate, 1,4-butanediol dimethacrylate, 1,6-hexanediol diacrylate, 1,6-hexanediol dimethacrylate, 1,2,4-butanetriol trimethacrylate, 1,4-cyclohexanediol diacrylate, 1,4-benzenediol dimethacrylate, pentaerythritol tri- and tetraacrylate/methacrylate, dipentaerythritol hexaacrylate, tripentaerythritol hexaacrylate, tripentaerythritol octacrylate, trimethylolpropane triacrylate, trimethylolpropane trimethacrylate, trimethylolethane triacrylate, sorbitol hexaacrylate, 1,3-propanediol diacrylate, 1,5-pentanediol dimethacrylate, 1,9-nonanediol dimethacrylate, 1,10-decanediol dimethacrylate, propylene glycol diacrylate, dipropylene glycol diacrylate, diacrylates and dimethacrylates of polyethylene glycol having a molar mass of 200 to 1500 g/mol. 1,4-Butanediol diacrylate, trimethylolpropane dimethacrylate, ethylene glycol dimethacrylate, and 1,6-hexanediol dimethacrylate are preferred and ethylene glycol dimethacrylate or 1,6-hexanediol dimethacrylate are particularly preferred. It is also possible to use mixtures of corresponding polyfunctional crosslinkers.

Suitable olefinically unsaturated acid-functional monomers d) are sulfonyl-, phosphate- or carboxyl-functional monomers, preference being given to carboxyl-functional monomers such as acrylic acid, methacrylic acid, β-carboxyethyl acrylate, crotonic acid, fumaric acid, maleic anhydride, itaconic acid or monoalkyl esters of dibasic acids/anhydrides such as, for example, monoalkyl maleate. Compounds useful as component d) further include unsaturated, free-radically polymerizable compounds having phosphate/phosphonate or sulfonyl/sulfonate groups, as described for example in WO-A 00/39181 (page 8, line 13-page 9, line 19). Acrylic acid and methacrylic acid are particularly preferred and acrylic acid is very particularly preferred.

Suitable esters e) of methacrylic acid comprise particularly methyl methacrylate, ethyl methacrylate, propyl methacrylate, isopropyl methacrylate, n-butyl methacrylate, sec-butyl methacrylate, tert-butyl methacrylate, pentyl methacrylate, hexyl methacrylate, heptyl methacrylate, octyl methacrylate, 2-octyl methacrylate, ethylhexyl methacrylate, nonyl methacrylate, 2-methyloctyl methacrylate, 2-tert-butylheptyl methacrylate, 3-isopropylheptyl methacrylate, decyl methacrylate, undecyl methacrylate, 5-methylundecyl methacrylate, dodecyl methacrylate, 2-methyldodecyl methacrylate, tridecyl methacrylate, 5-methyltridecyl methacrylate, tetradecyl methacrylate, pentadecyl methacrylate, hexadecyl methacrylate, 2-methylhexadecyl methacrylate, heptadecyl methacrylate, 5-isopropylheptadecyl methacrylate, 5-ethyloctadecyl methacrylate, octadecyl methacrylate, nonadecyl methacrylate, eicosyl methacrylate, cycloalkyl methacrylates, for example cyclopentyl methacrylate, cyclohexyl methacrylate, 3-vinyl-2-butylcyclohexyl methacrylate, cycloheptyl methacrylate, cyclooctyl methacrylate, bornyl methacrylate, tetrahydrofurfuryl methacrylate or isobornyl methacrylate. The methacrylic acid derivatives can further also be used in the form of the corresponding nitriles or amides, e.g., methacrylonitrile or methacrylamide. There is also the possibility of using other functional monomers according to the desired use, for example diacetone methacrylamide or acetoacetoxyethyl methacrylate. Methyl methacrylate, ethyl methacrylate, butyl methacrylate, and tert-butyl methacrylate are preferred and methyl methacrylate, tert-butyl methacrylate and butyl methacrylate are particularly preferred.

The polyacrylate suspension of the present invention is obtainable in a conventional manner, for example by emulsion polymerization.

The polymer particles in the polyacrylate suspensions of the present invention generally have an average particle size of 20 to 400 nm, preferably of 90 to 170 nm, and more preferably of 100 to 130 nm.

The solids content of an aqueous suspension is generally determined via the ratio of water to organic starting materials. The solids content of the polyacrylate suspension according to the present invention is preferably between 5 and 65 wt %, more preferably between 30 and 55 wt % and even more preferably between 35 and 45 wt %.

The aqueous suspension B) is typically in an amount of 1 to 50, preferably 5 to 30 and more preferably 5 to 25 wt % based on the solids content of the dispersion on the solids content of the final foam.

In a further preferred embodiment, the composition of the present invention may comprise A) heterocyclic 4-ring or 6-ring oligomers of low molecular weight aliphatic diisocyanates having a molar mass of 140 to 278 g/mol.

Examples of suitable oligomers C) are heterocyclic 4-ring or 6-ring oligomers of low molecular weight aliphatic diisocyanates having a molar mass of 140 to 278 g/mol such as isocyanurates, iminooxadiazinediones or uretdiones of the aforementioned low molecular weight aliphatic diisocyanates. Preference is given to heterocyclic 4-ring oligomers such as uretdiones. The increased isocyanate group content due to the use of component C) ensures better foaming, since more $CO_2$ is formed in the isocyanate-water reaction.

The composition of the present invention may also comprise

B) C8 to C22 monocarboxylic acids or ammonium or alkali metal salts thereof or C12 to C44 dicarboxylic acids or ammonium or alkali metal salts thereof or alkali metal salts of weak inorganic acids.

Examples of suitable compounds of component D) are the ammonium, sodium, lithium or potassium salts of ethylhexanoic acid, octanoic acid, decanoic acid, dodecanoic acid, palmitic acid, stearic acid, the octadecenoic acids, the octadecadienoic acids, the octadecatrienoic acids, isostearic acid, erucic acid, abietic acid and hydrogenation products thereof. Examples of $C_{12}$ to $C_{44}$ dicarboxylic acids and the ammonium and alkali metal salts derived therefrom are dodecanedioic acid, dodecenylsuccinic, tetradecenylsuccinic, hexadecenylsuccinic and octadecenylsuccinic acids, $C_{36}$ and $C_{44}$ dimer fatty acids and hydrogenation products thereof and also the corresponding ammonium, sodium, lithium or potassium salts of these dicarboxylic acids.

Alkali metal salts of weak inorganic acids for the purposes of the present invention are defined by their corresponding free acids having a $pK_A$ value of $\geq 4.0$ and $\leq 14.0$ in water at 25° C. Examples are potassium hydroxide, sodium hydroxide, potassium carbonate, sodium carbonate and sodium bicarbonate, although any mixtures of these salts are also suitable.

In yet a further preferred embodiment, the composition according to the present invention may comprise
C) hydrophilic polyisocyanates obtainable by reaction of
E1) aliphatic diisocyanates especially of molar mass 140 to 278 g/mol and/or polyisocyanates obtainable therefrom with an isocyanate functionality of 2 to 6, with
E2) monofunctional polyalkylene oxides especially of OH number 10 to 250 and an ethylene oxide fraction of 50 to 100 mol %, based on the total amount of oxyalkylene groups present.

The hydrophilic polyisocyanates E) can be prepared by adjusting the ratio of monofunctional polyalkylene oxides E2) to the aliphatic diisocyanates E1) such that for every 1 mol of OH groups of the monofunctional polyalkylene oxides there are from 1.25 to 15 mol, preferably from 2 to 10 mol and more preferably from 2 to 6 mol of NCO groups of the aliphatic diisocyanate E1). This is preferably followed by the allophanatization/biuretization and/or isocyanurate formation/uretdione formation. When the polyalkylene oxides E2) become bonded to the aliphatic diisocyanates E1) via urethane groups, it is preferably an allophanatization which takes place subsequently. It is further preferable for isocyanurate structural units to be formed.

An alternative way to prepare the hydrophilic polyisocyanates E) typically involves reacting 1 mol of OH groups of the monofunctional polyalkylene oxide component E2) with 1.25 to 15 mol, preferably with 2 to 10 mol and more preferably 2 to 6 mol of NCO groups of a polyisocyanate E1) having an isocyanate functionality of 2 to 6, based on aliphatic diisocyanates. Exemplary of such polyisocyanates E1) are biuret structures, isocyanurates/-uretdiones based on aliphatic diisocyanates. The polyisocyanate E1) and the polyalkylene oxide E2) are preferably linked together via a urethane group or a urea group, although particularly the linking via urethane groups is preferable.

The reaction can be carried out in the presence of urethanization catalysts such as tin compounds, zinc compounds, amines, guanidines or amidines, or in the presence of allophanatization catalysts such as zinc compounds.

The reaction temperature is typically in the range from 25 to 140° C. and preferably in the range from 60 to 100° C.

When excess low molecular weight diisocyanate was used, excess low molecular weight aliphatic diisocyanate is preferably subsequently removed, more preferably by thin film distillation.

Before, during and after the reaction or distillative removal of excess diisocyanate, acidic or alkylating stabilizers, such as benzoyl chloride, isophthaloyl chloride, methyl tosylate, chloropropionic acid, HCl or antioxidants, such as di-tert-butylcresol or tocopherol can be added.

The NCO content of the hydrophilic polyisocyanates E) is preferably in the range from 0.3 to 20 wt %, more preferably in the range from 2 to 10 wt % and most preferably in the range from 3 to 6 wt %.

Examples of low molecular weight aliphatic diisocyanates of component E1) are hexamethylene diisocyanate (HDI), isophorone diisocyanate (IPDI), butylene diisocyanate (BDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, of which hexamethylene diisocyanate, isophorone diisocyanate, butylene diisocyanate and bis(isocyanatocyclohexyl)methane are preferable. Hexamethylene diisocyanate, isophorone diisocyanate and butylene diisocyanate are more preferable and hexamethylene diisocyanate and isophorone diisocyanate are most preferable.

Examples of comparatively high molecular weight polyisocyanates E1) are polyisocyanates having an isocyanate functionality of 2 to 6 with isocyanurate, urethane, allophanate, biuret, iminooxadiazinetrione, oxadiazinetrione and/or uretdione groups based on the aliphatic and/or cycloaliphatic diisocyanates mentioned in the preceding section.

Preference for use as component E1) is given to comparatively high molecular weight compounds with biuret, iminooxadiazinedione, isocyanurate and/or uretdione groups based on hexamethylene diisocyanate, isophorone diisocyanate and/or 4,4'-diisocyanato-dicyclohexylmethane. Isocyanurates are more preferable. Structures based on hexamethylene diisocyanate are most preferable.

The monofunctional polyalkylene oxides E2) have an OH number of 10 to 250, preferably of 28 to 112, and an ethylene oxide fraction of 50 to 100 mol %, preferably of 60 to 100 mol %, based on the total amount of oxyalkylene groups present.

For the purposes of the present invention, monofunctional polyalkylene oxides are compounds which have only one isocyanate-reactive group, i.e., a group which can react with an NCO group.

Preparing polyalkylene oxides E2) by alkoxylating suitable starter molecules is literature known (e.g., Ullmanns Encyclopädie der technischen Chemie, 4th edition, volume 19, Verlag Chemie, Weinheim pp. 31-38). Suitable starter molecules are especially saturated monoalcohols such as methanol, ethanol, n-propanol, isopropanol, n-butanol, isobutanol, sec-butanol, diethylene glycol monobutyl ether and also aromatic alcohols such as phenol or monoamines such as diethylamine. Preferred starter molecules are saturated monoalcohols of the aforementioned kind. It is particularly preferable to use diethylene glycol monobutyl ether or n-butanol as starter molecules.

The monofunctional polyalkylene oxides E2) typically have number average molecular weights of 220 to 3700 g/mol, preferably of 500 to 2800 g/mol.

It is also preferable for the monofunctional polyalkylene oxides E2) to have an OH group as isocyanate-reactive group.

To speed urethane formation, the composition of the present invention may contain catalysts F). The catalysts in question are typically compounds with which a person skilled in the art is familiar from polyurethane technology. Preference here is given to compounds from the group consisting of catalytically active metal salts, amines, amidines and guanidines. Specific examples are dibutyltin dilaurate (DBTL), tin acetate, 1,8-diazabicyclo[5.4.0]undecene-7 (DBU), 1,5-diazabicyclo[4.3.0]nonene-5 (DBN), 1,4-diazabicyclo[3.3.0]octene-4 (DBO), N-ethylmorpholine (NEM), triethylenediamine (DABCO), pentamethylguanidine (PMG), tetramethylguanidine (TMG), cyclotetra-methylguanidine (TMGC), n-decyltetramethylguanidine (TMGD), n-dodecyltetramethyl-guanidine (TMGDO), dimethylaminoethyltetramethylguanidine (TMGN), 1,1,4,4,5,5-hexa-methylisobiguanidine (HMIB), phenyltetramethylguanidine (TMGP) and hexamethyleneoctamethylbiguanidine (HOBG).

Preference is given to the use of amines, amidines, guanidines or mixtures thereof as catalysts F). Preference is also given to using 1,8-diazabicyclo[5.4.0]undecene-7 (DBU).

In a particularly preferred embodiment of the present invention, catalysts are eschewed entirely.

Compounds of component G) can be used to improve foam formation, foam stability or the properties of the resulting polyurethane foam, in which case such additives can in principle be any known anionic, cationic, amphoteric and nonionic surfactants and also mixtures thereof. Preference is given to using alkylpolyglycosides, EO-PO block copolymers, alkyl or aryl alkoxylates, siloxane alkoxylates, esters of sulfosuccinic acid and/or alkali or alkaline earth metal alkanoates. Particular preference is given to using EO-PO block copolymers. Most preferably, EO-PO block copolymers are solely used as component G).

In addition, compounds of component H) can be used to improve the foam properties of the resulting polyurethane foam. These compounds comprise in principle any mono- and polyhydric alcohols known per se to a person skilled in the art, and also mixtures thereof. These are mono- or polyhydric alcohols or polyols, such as ethanol, propanol, butanol, decanol, tridecanol, hexadecanol, ethylene glycol, neopentyl glycol, butanediol, hexanediol, decanediol, trimethylolpropane, glycerol, pentaerythritol, monofunctional polyether alcohols and polyester alcohols, polyether diols and polyester diols.

Typically, components A) to H) are used in the following amounts:
100 parts by weight of isocyanate-functional prepolymer A)
0.1 to 200 parts by weight of aqueous suspension B)
0 to 30 parts by weight of heterocyclic oligomers C)
0 to 5 parts by weight of $C_8$ to $C_{22}$ monocarboxylic acids or ammonium or alkali metal salts thereof or $C_{12}$ to $C_{44}$ dicarboxylic acids or ammonium or alkali metal salts thereof or alkali metal salts of weak inorganic acids D)
0 to 250 parts by weight of hydrophilic polyisocyanate E)
0 to 1 part by weight of catalyst F)
0 to 10 parts by weight of surfactant G)
0 to 20 parts by weight of alcohol H)

Preferably, components A) to H) are used in the following amounts:
100 parts by weight of isocyanate-functional prepolymer A)
0.1 to 100 parts by weight of aqueous suspension B)
1 to 30 parts by weight of heterocyclic oligomers C)
0.01 to 5 parts by weight of $C_8$ to $C_{22}$ monocarboxylic acids or ammonium or alkali metal salts thereof or $C_{12}$ to $C_{44}$ dicarboxylic acids or ammonium or alkali metal salts thereof or alkali metal salts of weak inorganic acids D)
10 to 100 parts by weight of hydrophilic polyisocyanate E)
0 to 1 part by weight of catalyst F)
0 to 5 parts by weight of surfactant G)
0 to 10 parts by weight of alcohol H)

More preferably, components A) to H) are used in the following amounts:
100 parts by weight of isocyanate-functional prepolymer A)
1 to 60 parts by weight of aqueous suspension B)
5 to 15 parts by weight of heterocyclic oligomers C)
0.1 to 1 part by weight of $C_8$ to $C_{22}$ monocarboxylic acids or ammonium or alkali metal salts thereof or $C_{12}$ to $C_{44}$ dicarboxylic acids or ammonium or alkali metal salts thereof or alkali metal salts of weak inorganic acids D)
20 to 80 parts by weight of hydrophilic polyisocyanate E)
0 to 0.5 part by weight of catalyst F)
0 parts by weight of surfactant G)
0 parts by weight of alcohol H)

The present invention further provides a process for producing a hydrophilic aliphatic polyurethane foam, said process comprising a composition as claimed in the present invention being produced by mixing the components, foaming the mixture and curing the foamed mixture.

The hydrophilic aliphatic polyurethane foams of the present invention are typically obtained by mixing the components A), B), and optionally C), D), E), F), G), H) in any order, foaming the mixture and curing, preferably by chemical crosslinking. Components A), C) and E) are preferably premixed with one another. Optional carboxylates D) and optional surfactants G) are preferably added to the reaction mixture in the form of their aqueous solutions. Besides the water which is necessarily introduced via component B), further water can also be added.

Foaming can in principle be effected by means of the carbon dioxide formed in the course of the reaction of the isocyanate groups with water, but the use of further blowing agents is likewise possible. It is thus also possible in principle to use blowing agents from the class of the hydrocarbons such as $C_3$-$C_6$ alkanes, for example butanes, n-pentane, isopentane, cyclopentane, hexanes or the like, or halogenated hydrocarbons such as dichloromethane, dichloromonofluoromethane, chlorodifluoroethanes, 1,1-dichloro-2,2,2-trifluoroethane, 2,2-dichloro-2-fluoroethane, particularly chlorine-free hydrofluorocarbons such as difluoro-methane, trifluoromethane, difluoroethane, 1,1,1,2-tetrafluoroethane, tetrafluoroethane (R 134 or R 134a), 1,1,1,3,3-pentafluoropropane (R 245 fa), 1,1,1,3,3,3-hexafluoropropane (R 256), 1,1,1,3,3-pentafluorobutane (R 365 mfc), heptafluoropropane, or else sulfur hexafluoride. Mixtures of these blowing agents can also be used.

The subsequent curing typically takes place at room temperature.

After curing, any residual moisture still present can optionally be removed using customary methods such as, for example, convective air drying or microwave drying.

The present invention further also provides a polyurethane foam obtainable by the process according to the present invention and also for the use of said foam as means for treating wounds.

The polyurethane foam has a porous, at least partly open-cell structure comprising intercommunicating cells. The density of the polyurethane foam is typically in the range from 0.01 to 0.5 g/cm³ (determination to DIN 53420).

The absorbence for physiological saline on the part of the polyurethane foam is typically in the range from 25 to 150 g per 100 cm² for a foam 5 mm in thickness. The measurement is made according to the following method: (determination to DIN EN 13726-1 Part 3.2).

Compared with other hydrophilic foams, the polyurethane foam according to the present invention can be used to achieve a very high absorption of physiological saline even without the use of superabsorbent polymers. It will be appreciated, however, that incorporation of superabsorbents is also possible with the polyurethane foam according to the present invention.

The polyurethane foam generally has only a minimal water-extractable fraction of not more than 5 wt % and preferably of not more than 2 wt %; that is, they only contain very small amounts of chemically unbound constituents.

The polyurethane foam may additionally also be sterilized in a further operation. Sterilization is effected using processes known per se to one skilled in the art, wherein sterilization is effected by thermal treatment, chemical substances such as ethylene oxide or irradiation, for example by gamma irradiation. Irradiation here may be carried out under protective gas atmosphere, where appropriate. The polyurethane foam according to the invention here has the immense advantage of not discoloring on irradiation, in particular on irradiation with gamma rays.

It is likewise possible to add, incorporate or coat antimicrobially or biologically active compounds which have a positive effect in relation to wound healing and the avoidance of germ loads.

After production, the polyurethane foam can be made into sheetlike materials in a conventional manner and then can be used, for example, as a constituent of a wound dressing, of a cosmetic article or of an incontinence product. Generally, to this end, slab foams are cut to the desired thickness by common methods by means of which sheetlike materials having a thickness of typically from 10 μm to 5 cm, preferably from 0.1 mm to 1 cm, more preferably from 0.1 mm to 6 mm and most preferably from 0.2 mm to 6 mm, are obtained.

However, sheetlike foams can also be obtained directly using suitable casting techniques, by application and foaming of the composition according to the invention onto a substrate, for example an optionally pretreated paper or textile.

In a preferred version, the composition of the present invention is for this purpose applied to a substrate by blade coating whereupon, subsequent to the blade coating, the foaming up takes place. The gap height of the blade coater is generally in the range from 0.2 to 20 mm, preferably in the range from 0.5 to 5 and most preferably in the range from 0.8 to 2 mm. The film width of the blade coater to be used can be adapted to the particular purpose of use. Examples are film widths between 10 and 5000 mm and preferably between 20 and 2000 mm.

The polyurethane foams of the present invention are very useful for producing wound dressings. The present invention accordingly further provides a wound dressing comprising a polyurethane foam of the present invention.

In a particularly preferred embodiment of the wound dressing according to the present invention, said wound dressing includes a backing layer and/or an adhesive layer and/or a covering layer.

Suitable backing layers include, for example, films, foils, foams or membranes.

The backing layer may be constructed to be water vapor permeable within the meaning of DIN 53333 or DIN 54101.

The backing layer may preferably contain thermoplastic polymers, in the form of a coating for instance, or consist thereof. A thermoplastic polymer is initially a polymer which, when repeatedly heated and cooled in the temperature range typical for processing and using the material, remains thermoplastic. Thermoplastic is to be understood as referring to the property of a manufactured polymer of, in a temperature range typical for that manufactured polymer, repeatedly softening when hot and hardening when cold and, in the softened state, repeatedly being moldable into intermediate or final articles by flowing, as a molded, extruded or formed part for example.

Preferred thermoplastic polymers are polyurethane, polyethylene, polypropylene, polyvinyl chloride, polystyrene, polyether, polyester, polyamide, polycarbonate, polyether-polyamide copolymers, polyacrylate, polymethacrylate and/or polymaleate. The thermoplastic polymers are advantageously elastomeric. It is particularly preferable for the backing foil to contain or consist of thermoplastic polyurethane (TPU). Thermoplastic polyurethanes selected from the group comprising aliphatic polyester polyurethanes, aromatic polyester polyurethanes, aliphatic polyether polyurethanes and/or aromatic polyether polyurethanes are particularly suitable. These polymers can be used to obtain backing layers in the form of breathable elastic foil membranes. These are notable for high flexibility and elasticity over a wide temperature range, good imperviousness in respect of liquid water while at the same time being highly water vapor permeable, quietness, good textile haptics, durability to laundering and cleaning, very good chemical and mechanical resistance and freedom from plasticizer.

Particular preference is also given to a backing layer which acts as a barrier to germs and/or has high imperviousness with regard to wound exudate while at the same time being permeable to water vapor. To this end, the backing layer can be configured as a semipermeable membrane for example.

It is further advantageous for the backing layer to have a thickness in the range from ≥5 μm to ≤80 μm, especially from ≥5 μm to ≤60 μm and most preferably from ≥10 μm to ≤30 μm and/or a breaking extension of above 450%.

Suitable adhesive layers include, for example, pressure-sensitive adhesives based on polyurethane, silicone or acrylate.

Examples of polyurethane-based adhesives are hydrophilic polyurethane elastomers as described in EP 1 923 077 and EP 1 815 875 A1. Self-adhesive hydrophilic polyurethane gel foams known from WO 94/07935 are likewise suitable.

Suitable covering layers contain or consist of materials having minimal adherence to the adhesive of the adhesive layer when brought into contact therewith. Examples of such covering layers are release papers, which are coated with a non-adherent silicone or polyolefin layer.

The wound dressings of the present invention can be engineered such that the polyurethane foam in use is in direct or indirect contact with the wound in question. Preferably, however, the polyurethane foam is used in direct contact with the wound in order that optimum absorption of wound fluid may be ensured.

Exemplary constructions of wound dressings in which the polyurethane foam of the present invention can be used are described in EP 1 815 875, EP 1 923 077 or WO 98/17328.

EXAMPLES

Methods

Unless there are any indications to the contrary, percentages are all by weight.

Solids contents were determined to DIN-EN ISO 3251.

Viscosities were determined at 23° C. to DIN 53019.

NCO contents were determined volumetrically in accordance with DIN-EN ISO 11909.

Apparent density was determined by first measuring the width (B), height (H) and thickness (D) of a piece of foam and determining its mass (M). Apparent density was subsequently computed using the formula: apparent density=M/(B*H*D).

Volume swelling was determined by measuring a sheetlike piece of foam for its width ($B_{unswollen}$), height ($H_{unswollen}$) and thickness ($D_{unswollen}$), completely immersing the foam at room temperature (23° C.) in water for 2 minutes and subsequently measuring the width ($B_{swollen}$), height ($H_{swollen}$) and thickness ($D_{swollen}$) of the swollen foam. The volume swelling was then computed using the formula:

$$\text{Volume swelling (\%)} = (B_{swollen} * H_{swollen} * D_{swollen}) / (B_{unswollen} * H_{unswollen} * D_{unswollen}) * 100$$

"Free absorbency" was determined with regard to physiological saline in accordance with DIN EN 13726-1 Part 3.2.

Average particle sizes (the number average is reported) of polyurethane suspension 1 were determined using laser correlation spectroscopy (apparatus: Malvern Zetasizer 1000, Malver Inst. Limited).

Molecular weights were determined using gel permeation chromatography (GPC) as follows: Polystyrene standards having a molecular weights of Mp 1 000 000 to 162 were used for calibration. Tetrahydrofuran for analysis was used as eluent. The following parameters were maintained in the duplicate measurement: Degassing: online degasser; flow rate: 1 ml/min; analysis time: 45 minutes; detectors: refractometer and UV detector; injection volume: 100 µl-200 µl. Molar mass means $M_w$, $M_n$ and $M_p$ and the polydispersity $M_w/M_n$ were calculated with software support. Baseline points and evaluation limits were fixed in accordance with DIN 55672 Part 1.

The blade coater used was a Zehntner ZUA 2000 universal applicator having a film width of 200 mm and a gap height adjustable from 0 to 3 mm (from Zehntner GmbH, Sissach, Switzerland).

SUBSTANCES AND ABBREVIATIONS diaminosulfonate: $NH_2$—$CH_2CH_2$—$NH$—$CH_2CH_2$—$SO_3Na$ (45% strength in water)

Desmophen® C2200: polycarbonate polyol, OH number 56 mg KOH/g, number-average molecular weight 2000 g/mol (BayerMaterialScience AG, Leverkusen, DE)

PolyTHF® 2000: polytetramethylene glycol polyol, OH number 56 mg KOH/g, number-average molecular weight 2000 g/mol (BASF AG, Ludwigshafen, DE)

PolyTHF® 1000: polytetramethylene glycol polyol, OH number 112 mg KOH/g, number-average molecular weight 1000 g/mol (BASF AG, Ludwigshafen, DE)

Polyether LB 25: monofunctional polyether based on ethylene oxide/propylene oxide, number-average molecular weight 2250 g/mol, OH number 25 mg KOH/g (BayerMaterialScience AG, Leverkusen, DE)

Desmodur® N 3400: aliphatic polyisocyanate (HDI uretdione), NCO content 21.8%, Bayer MaterialScience AG, Leverkusen, Germany Desmodur® N 3300: aliphatic polyisocyanate (HDI isocyanurate), NCO content 21.8%, Bayer MaterialScience AG, Leverkusen, Germany Bayhydrol AH XP 2741: aqueous polyacrylate suspension, 41% solids content, Bayer MaterialScience AG, Leverkusen, Germany Dispercoll S4510: aqueous anionic colloidally disperse solution/suspension of amorphous silica, 50% solids content, particle size 55 nm, Bayer MaterialScience AG, Leverkusen, Germany Dispercoll S5005: aqueous anionic colloidally disperse solution/suspension of amorphous silica, 45% solids content, particle size 30 nm, Bayer MaterialScience AG, Leverkusen, Germany Preparation of Polyurethane Prepolymer 1
(Component A)

A mixture of 1000 g of hexamethylene diisocyanate (HDI) and 1 g of benzoyl chloride was admixed at 80° C. during 3 h with 1000 g of a polyalkylene oxide having a molar mass of 4680 g/mol started on glycerol, an ethylene oxide weight fraction of 72% and a propylene oxide weight fraction of 28% and dried beforehand at 100° C. during 6 h at a pressure of 0.1 mbar, by dropwise addition and subsequently stirred for 12 h. Excess HDI was removed by thin film distillation at 130° C. and 0.1 mbar, and the non-volatile constituents were stabilized with 1 g of chloropropionic acid. This gave a prepolymer having an NCO content of 2.77% and a viscosity of 3500 mPas.

Preparing the Hydrophilic Polyisocyanate
(Component E)

A mixture of 282.5 g of Desmodur N 3300 and 843.8 g of a hydroxyl-monofunctional polyether based on ethylene oxide/propylene oxide (having an ethylene oxide content of 80 mol based on the total amount of oxyalkylene groups present), number-average molecular weight 2250 g/mol and an OH number of 25 mg KOH/g was stirred in a glass apparatus at 80° C. until the titrimetrically determined NCO group content was constant. This gave a liquid having an NCO content of 4.04% and a viscosity of 3330 mPas.

Producing the Aqueous Polyurethane Suspension
(Component B)

1077.2 g of PolyTHF® 2000, 409.7 g of PolyTHF® 1000, 830.9 g of Desmophen® C2200 and 48.3 g of Polyether LB 25 were heated up to 70° C. in a standard stirred apparatus. A mixture of 258.7 g of hexamethylene diisocyanate and 341.9 g of isophorone diisocyanate was then added at 70° C. in the course of 5 min, followed by stirring at 120° C. until the theoretical NCO value was reached or the actual NCO value had dropped to slightly below the theoretical NCO value. The ready-produced prepolymer was dissolved with 4840 g of acetone, the solution was cooled down to 50° C. and then a solution of 27.4 g of ethylenediamine, 127.1 g of isophoronediamine, 67.3 g of diaminosulfonate and 1200 g of water was metered in over 10 min. The mixture was subsequently stirred for 10 min. This was followed by dispersal through addition of 654 g of water. The solvent was removed by distillation under reduced pressure.

The polyurethane suspension obtained had the following properties:

solids content: 61.6% average particle size: 528 nm pH (23° C.): 7.5

Producing the Polyurethane Foams

The two isocyanate components A) and E) were homogenized at a stirrer speed of 1200 rpm for 15 seconds and then the other components were added. The components were each used in the amounts reported in Table 1. Desmodur® N 3400 was in each case used as oligomer and a 5% solution of sodium oleate in water was used as carboxylate. Water added beyond that is specially indicated.

After the components had been mixed, the mixture was stirred for a further 10 seconds and the ready-produced composition was finally blade coated (gap height 1.5 mm) onto siliconized release paper. This is where the polyurethane foam developed.

To determine the volume swelling response, the foam was cut into smaller pieces. Apparent density, absorption and volume swelling were then determined as described in "Methods".

TABLE 1

| | Inventive Example 1 | Inventive Example 2 | Inventive Example 3 | Inventive Example 4 | Inventive Example 5 | Comparative Example 6* | Comparative Example 7* |
|---|---|---|---|---|---|---|---|
| prepolymer A) from Example 1 | 180 g | 180 g | 180 g | 180 g | 180 g | 180 g | 180 g |
| oligomer C) | 25 g | 25 g | 25 g | 25 g | 25 g | 25 g | 25 g |
| aqueous polyurethane suspension B) | 25 g | 87.5 g | | | | | |
| Bayhydrol AH XP 2741 B) | | | 30 g | | | | |
| Dispercoll S5005 | | | | 20 g | | | |
| Dispercoll S4510 | | | | | 80 g | | |
| water | | | | | | 10 g | 38 g |
| hydrophilic polyisocyanate E) | 45 g | 45 g | 45 g | 45 g | 45 g | 45 g | 45 g |
| sodium oleate E) as 5% solution in water | 24 g | 24 g | 24 g | 24 g | 8.5 g | 24 g | 24 g |
| Properties | | | | | | | |
| apparent density [g/1000 cm$^3$] | 140 | 193 | 193 | 132 | 173 | 131 | 191 |
| absorption [g/100 cm$^2$] | 72 | 55 | 57 | 70 | 61 | 99 | 73 |
| volume swelling (%) | 97 | 55 | 52 | 53 | 54 | 138 | 171 | oligomer: Desmodur N 3400
*comparative example without aqueous suspension, use of water The polyurethane foams of Examples 1, 2, 3, 4 and 5, obtained using the inventive compositions, displayed a very uniform, fine porous structure and pleasant, soft haptics. They also displayed high absorbence coupled with particularly low volume swelling. Such a combination of properties is unachievable with the known polyurethane foams. This is shown by comparing the inventive foams with those of comparative examples 6 and 7, which were obtained from compositions without an aqueous suspension.

The invention claimed is:

1. A composition consisting of
A) an isocyanate-functional prepolymer obtained by reacting
 A1) an aliphatic diisocyanate with
 A2) a di- to hexafunctional polyalkylene oxide having an ethylene oxide fraction of 50 to 100 mol %, based on the total amount of oxyalkylene groups present, and
B) an aqueous polyurethane suspension,
C) a heterocyclic 4-ring or 6-ring oligomers of low molecular weight aliphatic diisocyanates having a molar mass of 140 to 278 g/mol,
D) optionally C8 to C22 monocarboxylic acids or ammonium or alkali metal salts thereof or C12 to C44 dicarboxylic acids or ammonium or alkali metal salts thereof or alkali metal salts of inorganic acids,
E) a hydrophilic polyisocyanate obtained by reaction of
 E1) a low molecular weight aliphatic diisocyanate and/or a polyisocyanate obtained therefrom with an isocyanate functionality of 2 to 6, with
 E2) a monofunctional polyalkylene oxide of OH number 10 to 250 and an ethylene oxide fraction of 50 to 100 mol %, based on the total amount of oxyalkylene groups present,
F) optionally a catalyst,
G) optionally a surfactant, and
H) optionally a monohydric or polyhydric alcohol, wherein
the amounts of the components are as follows: 100 parts by weight of prepolymer A), 1 to 60 parts by weight of polymer suspension B), 5-15 parts by weight of oligomers C), and 20 to 80 parts by weight of hydrophilic polyisocyanate E),
and wherein the composition, when prepared as a foam, has a density of from 0.01 to 0.5 g/cm$^3$, and a water-extractable fraction of not more than 5 wt %.

2. The composition of claim 1, wherein the diisocyanate comprises an aliphatic diisocyanate having a molar mass of 140 to 278 g/mol.

3. The composition of claim 1, wherein the polyalkylene oxide has an OH number of 22.5 to 112.

4. The composition of claim 1, wherein said aqueous polymer suspension B) is an aqueous, hydrophilicized polyurethane suspension.

5. The composition of claim 1, wherein said aqueous polymer suspension B) is an aqueous, anionically hydrophilicized polyurethane suspension.

6. The composition of claim 5, wherein said aqueous, anionically hydrophilicized polyurethane suspension B) is obtained by preparing J) an isocyanate-functional prepolymer from
  J1) an organic polyisocyanate,
  J2) a polymeric polyol,
  J3) optionally a hydroxyl-functional compound, and
  J4) optionally an isocyanate-reactive, an anionic or potentially anionic and/or optionally a nonionic hydrophilicizing agent,
chain extending said isocyanate-functional prepolymer J) by complete or partial reaction of any free NCO groups with
  K1) an isocyanate-reactive agent, and/or
  K2) optionally an amino-functional compound,
and dispersing said prepolymer J) in water before, during or after said chain-extending reaction, wherein any potentially anionic groups present are converted into the anionic form by partial or complete reaction with a neutralizing agent.

7. A process for producing a hydrophilic aliphatic polyurethane foam, said process comprising producing the composition of claim 1 by mixing the components, foaming the mixture and curing the foamed mixture.

8. A polyurethane foam obtained by the process of claim 7.

9. A method for treating wound utilizing the polyurethane foam of claim 8.

10. A wound dressing comprising the polyurethane foam of claim 8.

11. The wound dressing of claim 10, comprising a backing layer and/or an adhesive layer and/or a covering layer.

12. The wound dressing of claim 11, wherein the polyurethane foam is at least regionally connected to the backing layer.

13. The wound dressing of claim 11, wherein the adhesive layer is at least regionally connected to the polyurethane foam and/or to the polyurethane foam side of the backing layer.

14. The wound dressing of claim 11, wherein the adhesive layer is at least regionally releasably connected to the covering layer.

15. A polymer system obtained by mixing said components A), B), C) and E) and optionally D), F), G), H) of the composition as claimed in claim 1.

16. The composition of claim 1, wherein the aliphatic diisocyanate A1) is hexamethylene diisocyanate, the aqueous polymer suspension B) is an aqueous, hydrophilicized polyurethane suspension, and wherein C) is a heterocyclic 4-ring oligomers.

* * * * *